US012172937B2

(12) United States Patent
Bloch et al.

(10) Patent No.: US 12,172,937 B2
(45) Date of Patent: Dec. 24, 2024

(54) NUTRIENT AND BIOCHAR PRODUCTION USING HIGH MOISTURE FEEDSTOCK AND BLACK SOLDIER FLIES

(71) Applicant: Intersect Agriculture, Inc., Cincinnati, OH (US)

(72) Inventors: John Bloch, Cincinnati, OH (US); Mark Mitchell, Terrace Park, OH (US); Nate Baldauf, Cincinnati, OH (US); Andrew Snorf, Cincinnati, OH (US)

(73) Assignee: Intersect Agriculture, Inc., Cincinnati, OH (US)

( * ) Notice: Subject to any disclaimer, the term of this patent is extended or adjusted under 35 U.S.C. 154(b) by 0 days.

(21) Appl. No.: 18/444,291

(22) Filed: Feb. 16, 2024

(65) Prior Publication Data

US 2024/0279133 A1 Aug. 22, 2024

Related U.S. Application Data

(60) Provisional application No. 63/446,206, filed on Feb. 16, 2023.

(51) Int. Cl.
*C05F 17/05* (2020.01)
*A01K 67/033* (2006.01)
(Continued)

(52) U.S. Cl.
CPC .............. *C05F 17/05* (2020.01); *A01K 67/033* (2013.01); *C05F 17/60* (2020.01); *C10B 53/00* (2013.01); *C10B 57/10* (2013.01)

(58) Field of Classification Search
None
See application file for complete search history.

(56) References Cited

U.S. PATENT DOCUMENTS

| 10,842,138 B1 | 11/2020 | Lolley |
| 2021/0137137 A1 | 5/2021 | Leo |
| 2023/0363395 A1* | 11/2023 | Andreola ............ C05F 3/00 |

FOREIGN PATENT DOCUMENTS

| CN | 110150234 | 6/2019 |
| CN | 110150234 A | 6/2019 |

(Continued)

OTHER PUBLICATIONS

International Search Report and Written Opinion for PCT/US24/16120 mailed Jul. 5, 2024, 7 pages.
(Continued)

*Primary Examiner* — Wayne A Langel
(74) *Attorney, Agent, or Firm* — Frost Brown Todd LLP; Vance V. VanDrake, III; Alexander J. Johnson (57) ABSTRACT

A closed-loop method for the continuous production of biochar and nutrients. High-moisture content feedstock and black soldier flies are placed within a breeding room to produce young black soldier fly larvae (BSFL). High-moisture content feedstock and a first portion of the young BSFL are placed within a growing room to produce leachate, mature BSFL, and frass. The mature BSFL can be separated from the frass and processed to produce dried BSFL, BSFL oil, BSFL meal, BSFL puree, or a combination thereof. A first portion of the frass undergoes pyrolysis to produce biochar and heat. The biochar can be utilized within the feedstock, to produce a frass end product, as a biochar end product, or a combination thereof. The heat can be utilized in the at least one breeding room, in the at least one growing room, to process the frass, or a combination thereof.

20 Claims, 6 Drawing Sheets

(51) Int. Cl.
  *C05F 17/60* (2020.01)
  *C10B 53/00* (2006.01)
  *C10B 57/10* (2006.01)

(56) References Cited

FOREIGN PATENT DOCUMENTS

| WO | 2016011541 A1 | 1/2016 |
| WO | WO 2016/011541 | 1/2016 |
| WO | WO 2022/118198 A2 | 6/2022 |

OTHER PUBLICATIONS

Notification of Transmittal of the Int'l Search Report and the Written Opinion of the Int'l Searching Authority from corresponding Int'l Application No. PCT/US24/16120, Jul. 5, 2024, ISA/US.

\* cited by examiner

NUTRIENT AND BIOCHAR PRODUCTION USING HIGH MOISTURE FEEDSTOCK AND BLACK SOLDIER FLIES

TECHNICAL FIELD

The present disclosure relates to the use of high moisture content feedstock and black soldier flies to produce useable nutrients in combination with the production of biochar.

BACKGROUND

Black soldier fly larvae (hereafter BSFL) are highly efficient at converting diverse sources of organic materials into biomass that can be fed to animals, including humans. Due to the high bioconversion rates and rapid consumption of organic waste, BSFL consumption results in direct food waste reductions, by weight, ranging from 44% to 82%. The remaining 56% to 18% of food waste inputs are mostly composed of frass excreted by the larvae as they metabolize food waste. Studies investigating frass composition and fertility have shown that BSFL frass can be a highly effective organic fertilizer. However, because of the copious quantities of material, a minimum 5-week typical requirement for composting the frass prior to sale on the market, and relatively low market value, raw frass can be a logistical challenge for many insect rearing companies, especially those with limited land that are located nearby sources of waste products for BSFL production.

BSFL frass can be converted to biochar through pyrolysis with the goal of sequestering carbon for hundreds of years, capturing waste heat for use in other steps of manufacturing process, and reducing the volume, weight, time, and logistical challenges associated with the production of huge quantities of frass from raising BSFL. Pyrolysis produces three major products: solid biochar, condensable gases, and non-condensable gases. Biochar is a charcoal-like product that may be highly porous. Biochar can be used to sequester carbon, to bind nutrients and pollutants in soils and water filtration and can be incorporated as a feed additive in animal diets. Condensable gases are composed of a complex mixture of hydrocarbons that can be combusted to produce heat or collected as pyrolysis oil through a cooling and condensation process. Non-condensable gasses include methane ($CH_4$) and hydrogen ($H_2$) gas that can also be combusted to produce heat energy.

By converting frass to biochar through pyrolysis, the weight of frass outputs can be reduced by more than 60% on a wet basis. The biochar can then be distributed or sold within five days of pyrolysis for incorporation into soils and other applications, as opposed to the 5 weeks of composting typically required for the raw frass to reach market. Pyrolyzing BSFL frass and combusting pyrolysis gases also generates excess heat that can be harvested to dry the wet frass prior to pyrolysis (from >20% to <20% moisture content) and heat growing rooms. Heat capture, together with the carbon sequestration of the biochar process, can make BSFL production and processing a net carbon negative nutrient production process.

The closed-loop process described herein: 1) uses high moisture (>50% moisture) industrial food processing waste materials including but not limited to spent grains, wet distillers grains, food waste, and other organic waste materials and by-products that are allowable in the US as primary feedstock for BSFL fed to animals; 2) requires nominal added water for production and processing of BSFL and biochar because of the high moisture content of the BSFL feedstock, a novel leachate collection system, a water collection and recycling system, a unique process for separating BSFL and frass that requires limited water, and a dry harvesting process; and 3) requires minimal added heat/energy to grow and process BSFL due to the capture and reuse of heat produced during the combustion of condensable and non-condensable pyrolysis gasses generated during the production of biochar.

BRIEF DESCRIPTION OF THE DRAWINGS

Various embodiments will become better understood with regard to the following description, appended claims and accompanying drawings wherein:

DETAILED DESCRIPTION

Various non-limiting embodiments of the present disclosure will now be described to provide an overall understanding of the principles of the structure, function, and use of the apparatuses, systems, methods, and processes disclosed herein. One or more examples of these non-limiting embodiments are illustrated in the accompanying drawings, wherein like numbers indicate the same or corresponding elements throughout the views. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment," or "in an embodiment" in places throughout the specification are not necessarily all referring to the same embodiment. Furthermore, the particular features, structures or characteristics may be combined in any suitable manner in one or more embodiments.

The examples discussed herein are examples only and are provided to assist in the explanation of the apparatuses, devices, systems, and methods described herein. None of the features or components shown in the drawings or discussed below should be taken as mandatory for any specific implementation of any of the apparatuses, devices, systems, or methods unless specifically designated as mandatory. For ease of reading and clarity, certain components, modules, or methods may be described solely in connection with a specific figure. Any failure to specifically describe a combination or sub-combination of components should not be understood as an indication that any combination or sub-combination is not possible. Also, for any methods described, it should be understood that unless otherwise specified or required by context, any explicit or implicit ordering of steps performed in the execution of a method does not imply that those steps must be performed in the order presented but instead may be performed in a different order or in parallel.

The present disclosure teaches a closed-loop process that uses high moisture content industrial food processing waste materials including, but not limited to, spent grains, wet distillers' grains, food waste/by-products, and other organic waste materials as the primary feedstock. Within the context of the present disclosure, the phrase high moisture content refers to waste materials having a greater than 50% moisture content prior to being utilized within the process of the present disclosure. The present disclosure requires nominal added water for production and processing of the BSFL and biochar because of the high moisture content of the BSFL feedstock. The present disclosure also utilizes a leachate collection system, a water collection and recycling system, a process for separating the BSFL and the frass that requires limited water, and a dry harvesting process. Additionally, the present disclosure requires minimal added heat/energy to grow and process the BSFL due to the capture and reuse of heat produced during the combustion of condensable and non-condensable pyrolysis gasses generated during the production of biochar.

Black soldier flies refer to the species *Hermetia illucens*. Within the context of the present disclosure, black soldier fly eggs refer to the egg stage of the black soldier fly life cycle. Within the context of the present disclosure, black soldier fly larvae (BSFL) refer to the larval portion of the black soldier fly life cycle, which follows the egg stage, precedes the pupal stage, and includes six instar stages. Within the context of the present disclosure, immature BSFL refers to BSFL instars one through five, with the sixth instar representing mature BSFL. Within the context of the present invention, mature BSFL refers to the sixth instar, or prepupal stage, of the black soldier fly life cycle. Within the context of the present disclosure, adult black soldier flies refer to the adult stage, following pupation, of the black soldier fly during which breeding takes place.

In a very first step of the method of the present disclosure, a source of black soldier flies may need to be provided. This can be in the form of black soldier fly eggs, BSFL, adult black soldier flies, or a combination of the above. If adult black soldier flies are the first source, then the system of the present disclosure can provide the perfect environment for the black soldier flies to breed and produce more BSFL. If the first source is either black soldier fly eggs or BSFL, they can then grow into adult black soldier flies, which can breed and produce more BSFL, a portion of which can then be reintroduced into the system of the present disclosure such that additional sources of BSFL or adult black soldier flies are not needed to continuously run the system.

Figure 1:
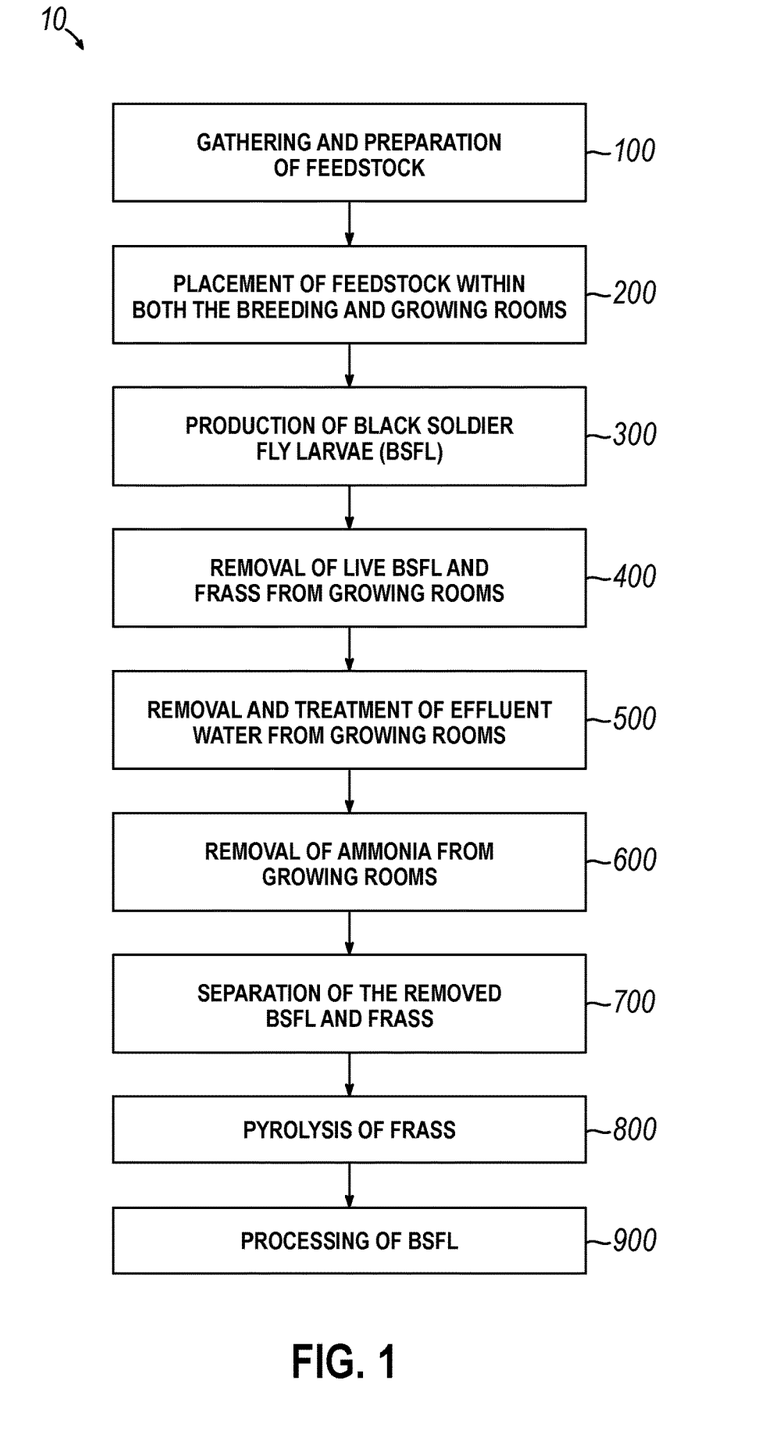
FIG. 1 is a process flow for the method of the present disclosure.
Figure 2:
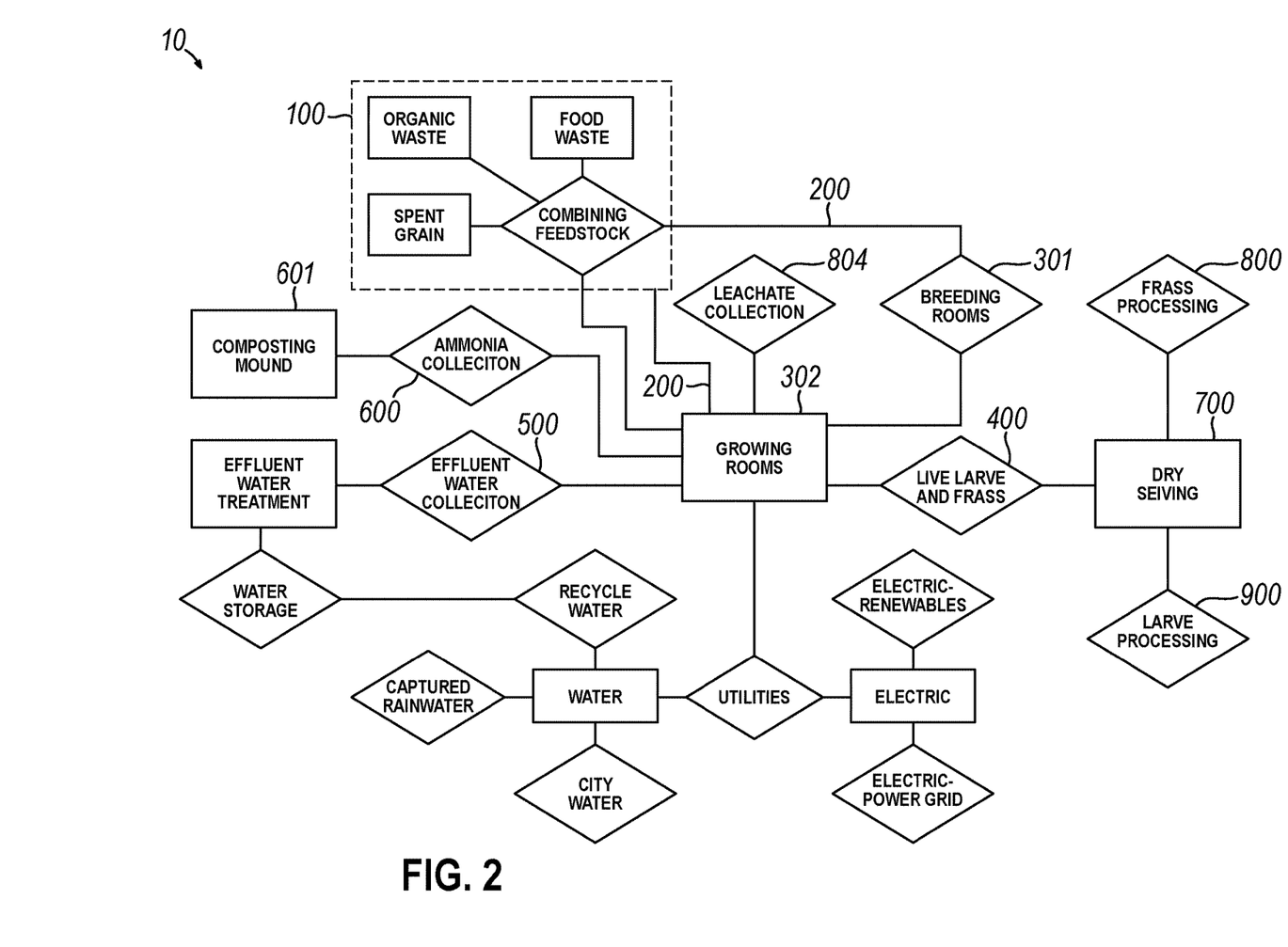
FIG. 2 is a schematic diagram of the method of the present disclosure.

FIG. 1 shows a flow chart of the major steps of the method 10 of the closed loop process of the present disclosure while FIG. 2 shows a schematic diagram of the production process flow of the method 10. A first step in the method 10 of the present disclosure may be gathering and preparing 100 of the feedstock used to feed the BSFL. In one or more embodiments, the feedstock can include organic waste materials, food waste material, spent grain, and combinations thereof. Once BSFL used for breeding and maintaining the population are sufficiently fed and mature, they may pupate, emerge as adults, and mate to produce eggs, which may hatch to become BSFL. These newly hatched BSFL can consume the feedstock and grow. A small portion (less than about 2%) of these newly hatched BSFL produced within the system of the present disclosure may then mature and breed with one another to produce more BSFL in a continuous circle. The rest of the newly hatched BSFL may then be moved from the breeding rooms to the growing rooms. This occurs after the BSFL spend several days feeding in small trays on high quality feedstock (e.g., chicken feed with or without other feedstock such as, but not limited to, spent grain). It may be in the growing rooms where the BSFL are cultivated for their use in finished products, as discussed in more detail below. In one or more embodiments, the feedstock used to feed the BSFL in the growing rooms may be a combination of spent grain, organic waste, and food waste. In one or more embodiments of the present disclosure, as discussed in detail below, the method of the present disclosure may eventually produce biochar. In one or more embodiments, a portion of the biochar produced can be recycled back into the feedstock to further enhance the feedstock.

Once the feedstock has been gathered and prepared, it can be placed within both the breeding rooms and the growing rooms in a second step 200. In one or more embodiments, feedstock in the breeding rooms may ideally be amended with chicken feed and/or other high-quality sources of feed to better fuel BSFL growth. This additional material can translate into better adult black soldier fly breeding success and a better production of a sufficient amount of eggs to sustain BSFL populations for the growing rooms. It can be within the breeding and growing rooms that the feedstock can be consumed by the BSFL as discussed above.

In one or more embodiments of the present disclosure, the system of the present disclosure can be powered by heat and electricity generated from a pyrolysis process discussed in detail below. In addition to the surplus heat collected from the pyrolysis process of the present disclosure, the system of the present disclosure can also use renewable energy sources. Energy from pyrolysis and renewable sources discussed above can be used to power the lights, heating sources, and cooling sources that are found within the breeding and growing rooms. This energy can also be used through the system of the present disclosure to assist in cleaning the production and processing areas of the system discussed in detail below. In one or more embodiments, the system of the present disclosure may also pull electricity from any available power grid and/or water from the local municipality in which the system resides.

Once the feedstock has been placed within the breeding and growing rooms, the production of BSFL can take place in a third step 300, as discussed above. In one embodiment of the present disclosure, the third step 300 may utilize a plurality of breeding and growing rooms. While it may be contemplated that both the actions of breeding and growing can take place within the same room, in other embodiments it can be envisioned that the breeding takes place in a separate breeding room(s) 301, and the growing takes place within a separate growing room(s). In one or more embodiments, the breeding can take place in vertical breeding cages that may be equipped with trays. The breeding cages may be lighted, temperature controlled, and humidity controlled to provide the optimal breeding conditions. Separate units can be used for pupation and breeding, or pupation and breeding can take place within the same lighted case for simplicity. Once the pupation, subsequent breeding, and egg laying take place, the eggs are transported to separate units in trays for hatching. Following hatching, the young BSFL may spend several days (from about 1 day to about 6 days) in vertically stacked trays before they are moved to a growing room(s) 302 which may contain vertical growing cages equipped with a net layer as discussed in further detail below. In one or more embodiments, the net layer may be a semipermeable net or an impermeable net.

As the young BSFL consume the high moisture content feedstock, they exude leachate. Leachate is the liquid waste released from the BSFL as they digest the feedstock. The leachate combines with gravitational water from the high moisture content feedstock and percolates through the net layers of the vertical growing cages found in the growing rooms 302 on to lower layers of feedstock and BSFL. In one or more embodiments, the net layers are specifically semipermeable mesh layers. While much of the moisture in the feedstock and produced leachate may become water vapor in the warm environment of the growing rooms, this water vapor also works to increase the humidity and therefore assists in improving the environmental conditions for BSFL production. However, in some embodiments, the environment of the growing rooms may need to be cooled in the later phases of BSFL development to condense the water vapor for leachate collection. Ultimately however, the leachate may flow into a collection system and then into a storage tank, such as storage tank 804. The leachate may then be held in storage until it can be transported to a biochar production area.

Once the growing process has taken place, which can occur over a period of from 8 days to 15 days, the mature BSFL and frass produced are removed from the growing rooms in a fourth step 400 and the two components are separated using a separation system, such as cyclonic separation or sieves. Within the context of the present disclosure, frass is the excrement produced by the BSFL as they eat the feedstock.

In a fifth step 500, once the breeding and growing rooms have been cleaned, as discussed in detail below, the water used to clean the rooms can be collected and it can be treated and recycled. This treated effluent water can then be used to clean the breeding and growing rooms in subsequent cycles of the process 10 of the present disclosure. The effluent water used in the cleaning processes may be directed through floor drains and into a treatments system for further processing such that it can again be used to clean the system of the present disclosure. In one or more embodiments, the treatment systems may include biological processes, chemical processes, physical processes, or combinations thereof. In one embodiment, the treatment system may be a biochar-based filtration system which utilizes cooled biochar produced from the system of the present disclosure. In one or more embodiments, water for use in the method 10 can come from precipitation collected using gutters flanking the exterior of the building or buildings that house the breeding room(s) 301 and the growing room(s) 302.

In a sixth step 600, ammonia may be removed from the system of the present disclosure. During the BSFL breeding and growing process, substantial amounts of ammonia are produced as a byproduct. This ammonia can be collected using ductwork placed in the breeding room(s) 301 and the growing room(s) 302. In one or more embodiments, the ductwork routes and pumps the ammonia to a composting mound 601 located adjacent the system of the present disclosure. The composting mound 601 utilizes biotic and abiotic processes to remove the ammonia. In one or more embodiments, biochar produced by the system of the present disclosure can be cooled and incorporated into the composting mound 601 to sorb ammonium and improve the ammonia removal efficiency of the composting mound 601. In one or more embodiments of the present disclosure, the composting mound 601 can be vegetated and the plants produced from the composting mound 601 can be harvested regularly to maintain an ammonium sink while also producing additional saleable products and/or additional feedstock to be utilized within the system of the present disclosure. In one or more embodiments, composting mound 601 can include soil, wood chips, vegetation, or combinations thereof.

In a seventh step 700, the BSFL and the frass are separated. In one or more embodiments, the BSFL and frass may be separated using a combination of air flow, heat, and light with agitation in a pre-heating tunnel. This separation activity encourages the BSFL to burrow down into a collection system away from heat and light, as BSFL prefers colder and darker environments. The use of air flow, heat, and light will also allow the frass to begin drying in preparation for pyrolysis or other end uses of the frass.

Once removed, the process of the present disclosure can utilize the frass in multiple diverse ways. The frass can simply be utilized as an end-product and can be sold for use as a soil amendment. The frass can also be processed further prior to undergoing pyrolysis for the production of biochar. If utilized as an end-product for sale, the frass can be composted, dried, and/or sold fresh. In one embodiment, the present disclosure contemplates that biochar produced from the method can be combined or composted with the frass to further enhance the frass for sale. In yet other embodiments, the frass can undergo an aerobic digestion step to be processed into an enhanced soil amendment. Aerobic digestion is a microbially-mediated process that requires oxygen and works to reduce the moisture content and volume of the frass. Aerobically digested frass could then be sold as a product or combined with biochar and/or leachate for sale. In yet another embodiment, aerobic digestion could also be used to process post-consumer waste feedstocks prior to feeding to black soldier flies in step 200 discussed above. If used to produce biochar, the frass may be pressed or centrifuged to remove any additional leachate, which can be collected and combined with the leachate collected in the third step 300. This reduced moisture frass can then be dried on its own or combined with external waste/by-products such as sawdust, woodchips, corrugated cardboard, or other organic materials and dried using heat generated during the pyrolysis process to have between about a 15% to about a 30% moisture content prior to pyrolysis. In one or more embodiments, the moisture content prior to pyrolysis can be about 20%.

In an eighth step 800, the prepared frass, alone or in combinations with other amendments as discussed above, undergoes pyrolysis. Pyrolysis is defined as the process of subjecting substances to highly elevated temperatures in relatively inert atmospheres in order to facilitate their thermal decomposition. The process of pyrolysis brings about a chemical change in the substance subjected to it (the chemical compositions of the initial reactant feedstock and the final product are different). Generally, substances that are subjected to pyrolysis undergo a chemical decomposition reaction and break down into multiple product compounds. The process of pyrolysis can be used to break down organic substances. For example, the charring of wood (or the incomplete combustion of wood) that results in the formation of charcoal involves the process of pyrolysis. Typically, the pyrolysis of an organic substance can produce multiple volatile products and may also leave behind a solid residue which can often be highly enriched with carbon. It can be noted that extreme pyrolysis, which often leaves only carbon as a residue, may also be commonly known as carbonization. It can also be noted that pyrolysis may be widely considered as the initial step for other related processes such as combustion and gasification.

In one or more embodiments, an initial supply of natural gas or other energy source may be required to initiate pyrolysis. Frass pyrolysis produces hot biochar, condensable gases, and non-condensable gases. The hot biochar produced may be allowed to cool before being combined with leachate. Leachate, treated effluent water, municipal water, or a combination thereof can be used to cool the hot biochar. In one or more embodiments, the condensable and non-condensable gases are burned in a separate chamber with oxygen to produce heat that may be captured using a heat-exchanger. In one or more embodiments, the captured heat can be directed to a pre-pyrolysis drying unit, the breeding room(s) 301 and the growing room(s) 302, to be utilized in the larvae processing discussed below, or as a renewable energy source to produce electricity as discussed above.

Figure 3:
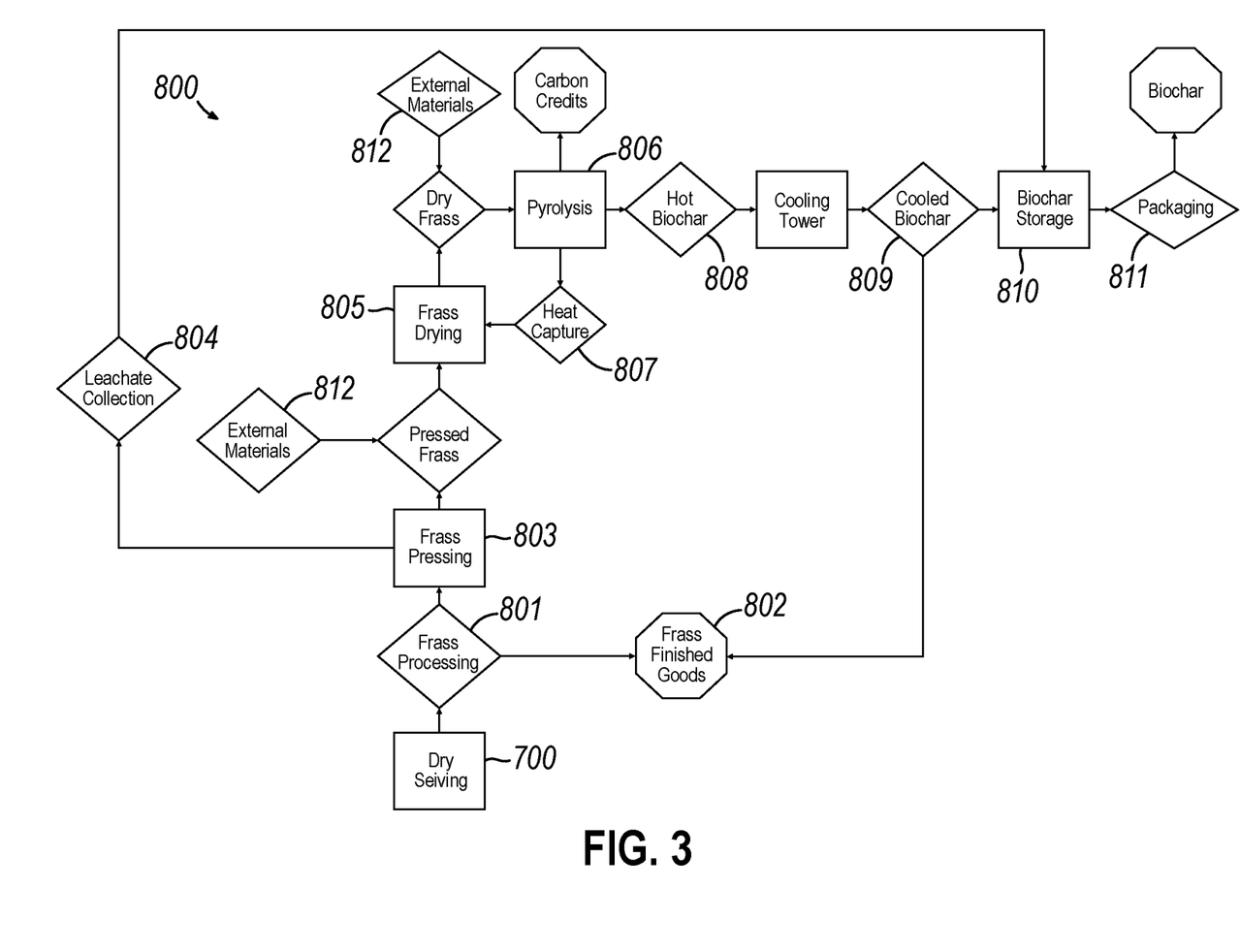
FIG. 3 is a schematic diagram of the pyrolysis step of the method of the present disclosure.

FIG. 3 breaks down the eighth step 800 in more detail. Once the frass has been separated from the live larvae in step 700, it can then be processed in a step 801. Processing of the frass entails separating a portion of the frass 802 to be utilized in frass finished goods and then utilizing the rest of the collected frass to be pressed at a step 803 so that it can ultimately be used in the pyrolysis process. During the pressing process at step 803, additional leachate may be collected and can be sent to the leachate collection tank 804. In one or more embodiments, instead of or in addition to pressing the frass at 803, the frass can be centrifuged or pressed to remove additional leachate. The pressed and/or centrifuged frass then goes through a drying step at 805. This dried frass can then undergo the pyrolysis process at a step 806. The pyrolysis production may produce heat, and this heat can be captured at 807 and used for several purposes within the process 10 as discussed above.

One such use of the captured heat 807 can be to have it assist in the drying step 805. As a result of the pyrolysis process at step 806, hot biochar 808 can be produced. This hot biochar 808 can then be placed within a cooling tower to produce cooled biochar 809. The hot biochar 808 can be cooled within the cooling tower by the addition of collected leachate stored in the collection tank 804 or in other embodiments, by the addition of water or a combination of water and collected leachate. In one or more embodiments, the source of water to the cooling tower can come from the water effluent collection step 500 discussed above. This cooled biochar 809 can then be sold as is or used within the closed loop method 10 of the present disclosure.

The cooled biochar 809 can be worked into the frass finished goods product 802 or it can be placed in a storage tank 810 for use as an end production good. In one or more embodiments, the cooled biochar can be milled into finer particles prior to storage within the storage tank 810. The cooled biochar stored in the storage tank 810 can be combined with leachate stored in the collection tank 804 to enhance the nutrient content of the biochar end product. The leachate added to the cooled biochar in storage tank 810 may assist in biochar quenching and nutrient sorption. Once combined with the leachate, the cooled biochar can then be packaged at a step 811 and used as a finished good product. In one or more embodiments, the pressed or centrifuged frass produced at step 803 can be combined with dry and/or carbon rich external materials 812 such as sawdust, woodchips, corrugated cardboard, or other organic materials. These external materials 812 may assist in supplying more carbon for sequestration in the biochar while also increasing the production of pyrolysis gases that can be used to generate additional heat through combustion, which can be collected at 807. The incorporation of these additional dry, carbon-rich external materials 812 also reduces the overall water content of the pyrolysis feedstock and therefore frees up heat typically required for pre-pyrolysis drying at 805.

In one or more embodiments, a portion of the frass to be combined with the cooled biochar can be soaked in water for several hours prior to being combined with the cooled biochar. This process may extract additional nutrients from the frass and adsorb these nutrients to the biochar for sale as a finished product. Additionally, in one or more embodiment, prior to being combined with frass, the cooled biochar can be micronized (crushed into microscopic particle size) in a mill to increase surface area, and the resulting solution after removal of the soaked frass could be used as a fertilizer spray since the small particle size of the biochar may allow the solution to be utilized in a spray-form. In one or more embodiments, the water the frass soaks in can come from the effluent water collected and processed at a fifth step 500 discussed above.

In a ninth step 900, the BSFL that was separated from the frass as discussed above can be processed. The separated BSFL can be utilized as a live finished product or dispatched quickly and processed using minimal water by shredding, freezing, and/or any a drying process such as microwave heating processes, fluidized bed drying, hot air drying, or infrared. The dispatched larvae may then be used as a wet saleable product or dried using heat captured from pyrolysis as discussed above. The dispatched and dried BSFL can then be packaged for sale, milled, and/or defatted for production of high protein meal, and/or high fat BSFL oil, and/or BSFL puree.

Figure 4:
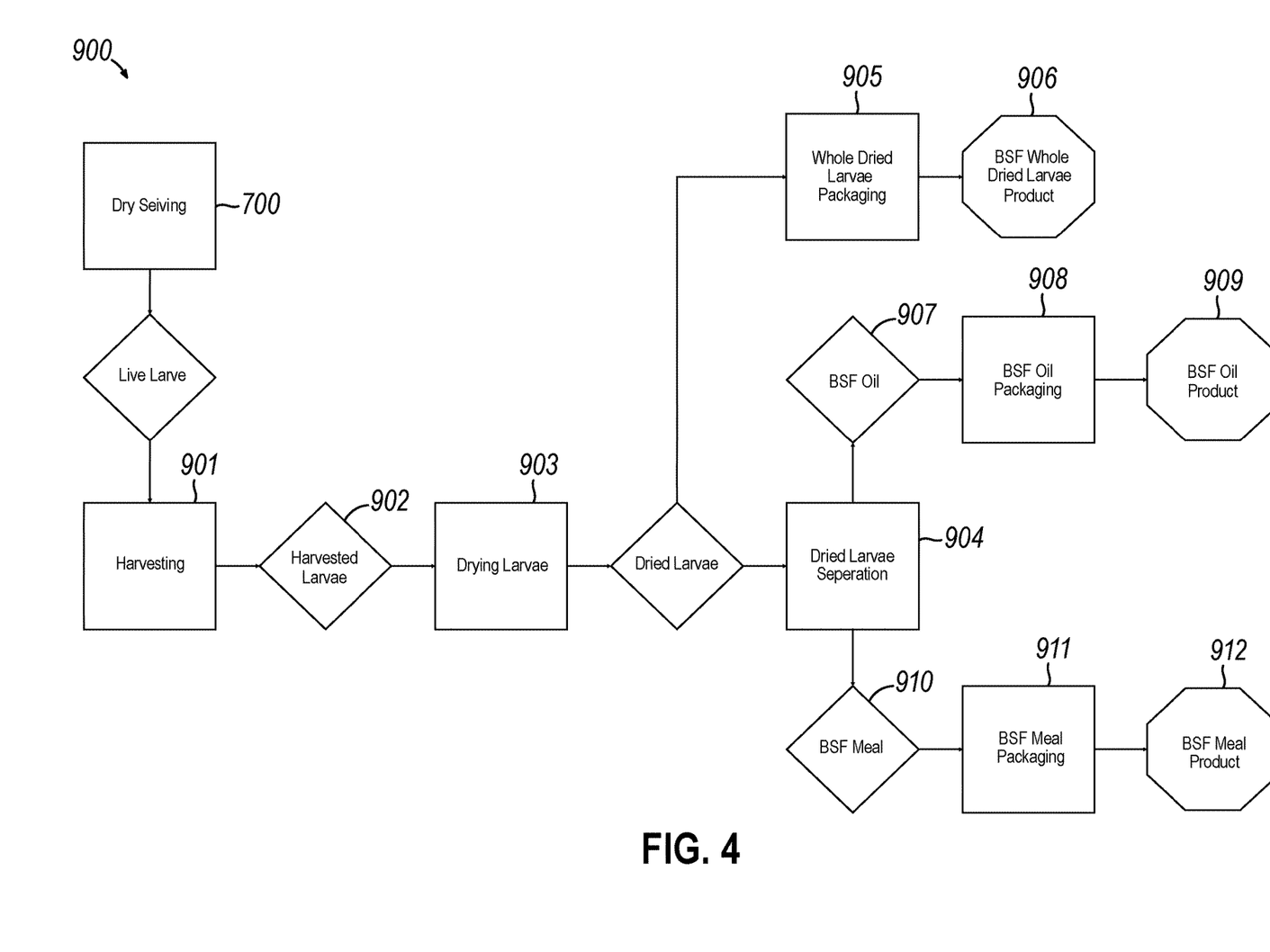
FIG. 4 is a schematic diagram of the BSFL processing step of the method of the present disclosure.

FIG. 4 breaks down the ninth step 900 in more detail. Once the BSFL has been separated from the frass in step 700, the BSFL can be harvested in a step 901. Harvesting of the BSFL entails separating a portion of the BSFL to be used as a live finished product 902 and then the rest of the harvested BSFL can be humanely dispatched at a step 903. In one or more embodiments, the BSFL can be humanely dispatched at a step 903 using minimal water and/or a microwave heating process. In one or more embodiments, the water utilized to dispatch the BSFL can come from the effluent water collected and processed at a fifth step 500 discussed above. The dispatched BSFL can then be separated at a step 904 to then be utilized to produce a number of packaged goods products.

In one embodiment, all of or a portion of the dispatched BSFL can be kept whole and packaged at a step 905 to produce a BSFL dried product 906. In one or more embodiments, all of or a portion of the dispatched BSFL can be defatted at a step 907. Step 907 may produce a high-fat BSFL oil that can be packaged at a step 908 and then sold as a BSFL oil product 909. In one or more embodiments, all of or a portion of the dispatched BSFL can be milled at a step 910. Step 910 may produce a BSFL meal which can then be packaged at a step 911 and then sold as BSFL meal product 912.

Figure 5:
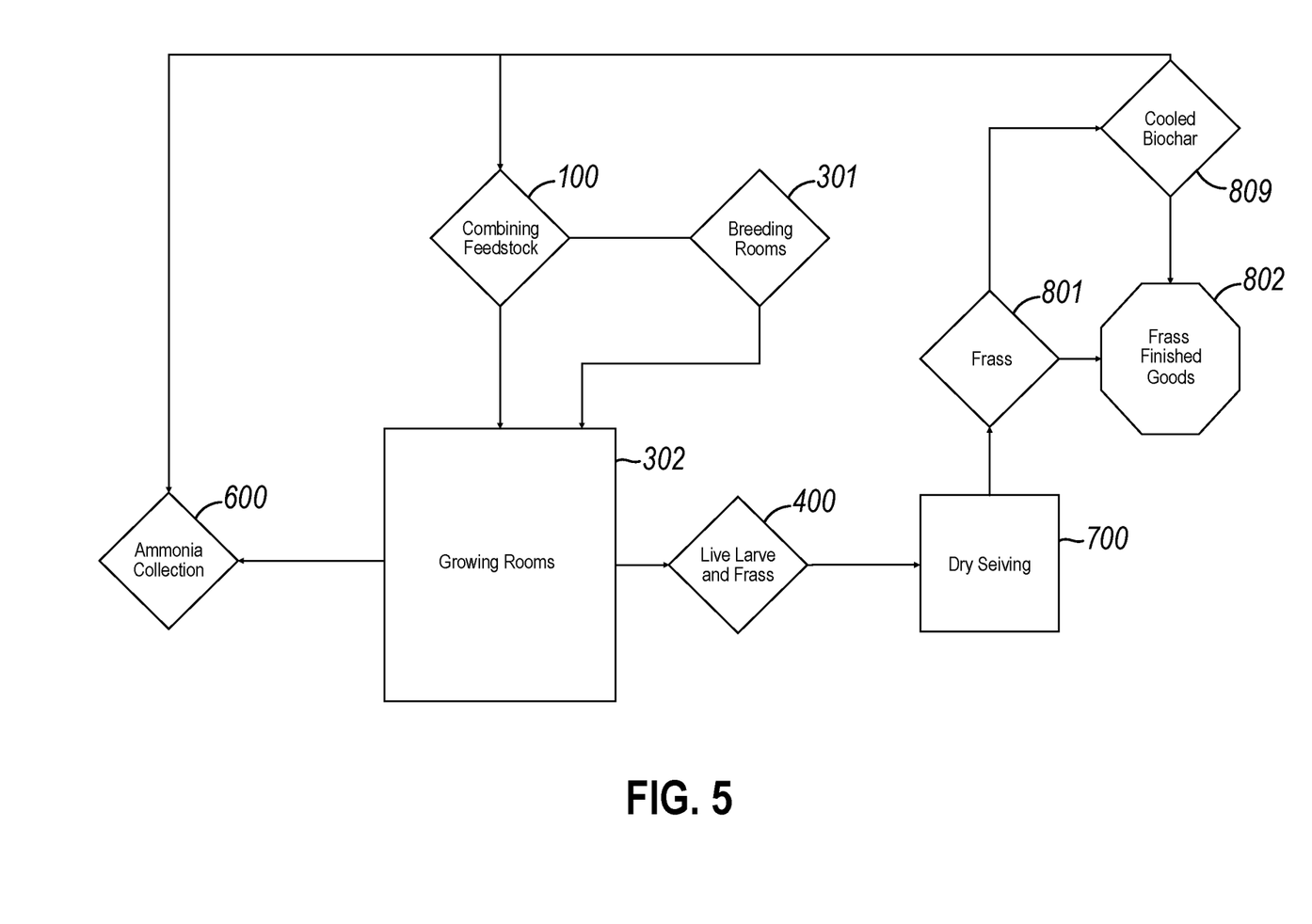
FIG. 5 is a schematic diagram of how the cooled biochar produced within the method of the present disclosure can be recirculated within the closed loop of method of the present disclosure.

FIG. 5 breaks down how the cooled biochar produced at step 809 can be recirculated within the closed loop of method 10. As discussed above, cooled biochar produced at step 809 can be added to composting mounds within the ammonia collection step 600 to improve the ammonia removal efficient through ammonium sorption. As also discussed above, in addition to being stored for additional use, the cooled biochar 809 can be worked into the frass finished goods product 802. In addition, as previously discussed above, the cooled biochar can be mixed into the feedstock prepared in step 100 to be used within the breeding room(s) 301 and the growing room(s) 302 to improve the BSFL yields.

In one or more embodiments of the present disclosure, placement of the feedstock within the breeding room(s) 301 and the growing room(s) 302 which takes place during step 200 can be accomplished through the use of an automated filler. In one or more embodiments, the automated filler has a self-lifting construction, such that the automated filler can be raised or lowered to reach each level of the vertically stacked rows of shelves. In one or more embodiments, the automated filler can also load directly from its automated belt onto the net layer of each level of the vertically stacked rows of shelves. In one or more embodiments, the automated filler can load at variable filling speeds.

In combination with the automated filler, one or more embodiments of the present disclosure can utilize an automated net puller for assistance with the loading of the feedstock within the growing room(s) 302 which takes placed during step 200. The automated net puller can be placed at the first end of each level of the vertically stacked rows of shelves, while the automated filler can be placed at the second end. As the automated filler loads feedstock onto the net layer at the second end, the automated net puller can pull the net layer along the length of each level, such that the filled net layer can be placed across the entire length of each level. In one or more embodiments, similar to the automated filler, the automated net puller has a self-lifting construction, such that the automated net puller can be raised or lowered to reach each level of the vertically stacked rows of shelves in the growing room(s) 302.

In one or more embodiments, the present disclosure may also utilize an automatic emptying unit for assistance with the emptying of the vertical growing cages within the growing room(s) 302 discussed above. The automatic emptying unit can be used to transport the used feedstock, frass, and BSFL from the vertical growing cages within the growing room(s) 302. The automatic emptying unit can be placed at an end of each level of the vertically stacked rows of shelves and can pull the net layer from each level, and all the used feedstock, frass, and BSFL located on said net layer at each level. In one or more embodiments, the automatic emptying unit may utilize a net pulling device to pull and secure the net layer, and an emptying conveyor to catch the used feedstock, frass, and BSFL.

In one or more embodiments, once the net layer from each level has been removed by the automatic emptying unit, the net layers can be transferred to an automatic washing unit. The automatic washing unit may not only wash and clean the net layers for reuse within the system of the present disclosure, but it may also take in and wind the net layer on a rod inside the automatic washing unit. This can add to the cleanliness of the net layers because the net layer may not touch the floor after being properly washed. In one or more embodiments, the water utilized to wash the net layers can come from the effluent water collected and processed at a fifth step 500 discussed above.

In one or more embodiments, the present disclosure can utilize an automatic mixing unit which can be utilized within each level of the vertically stacked rows of shelves to mix up the feedstock and the BSFL growing/feeding within the feedstock.

In one or more embodiments, the present disclosure can utilize an automatic shelve cleaning unit which can be utilized to clean each level of the vertically stacked rows of shelves once the net layer, used feedstock, frass, and BSFL have been removed from each level of the vertically stacked rows of shelves. In one or more embodiments, the water utilized to wash each level of the vertically stacked rows of shelves can come from the effluent water collected and processed at a fifth step 500 discussed above.

The concept of breeding within the confines of the present disclosure relates to a small percentage of BSFL which are allowed to mature and pupate into adult black soldier flies before mating with one another. Once mating occurs, each female may lay about 500 eggs. These eggs can hatch and spend 1 to 6 days within the confines of the nursery trays within the breeding room(s) 301 discussed above. After the 1-to-6-day period, the majority of the young larvae are then transported to the growing room(s) 302. In one or more embodiments, roughly 1 to 2 percent of the BSFL within the growing room(s) 302, are transported back to the breeding room(s) 301 to continue to feed on feedstock, in one or more embodiment the feedstock has also been amended with chicken feed or other high-quality feeds to encourage rapid growth and breeding success. Back within the growing room(s) 302, the BSFL are allowed to grow for approximately 9 days. After this approximate 9-day period in the growing room(s) 302, the roughly 14-day old BSFL are then removed from the growing room(s) 302 as discussed above at step 400.

Figure 6:
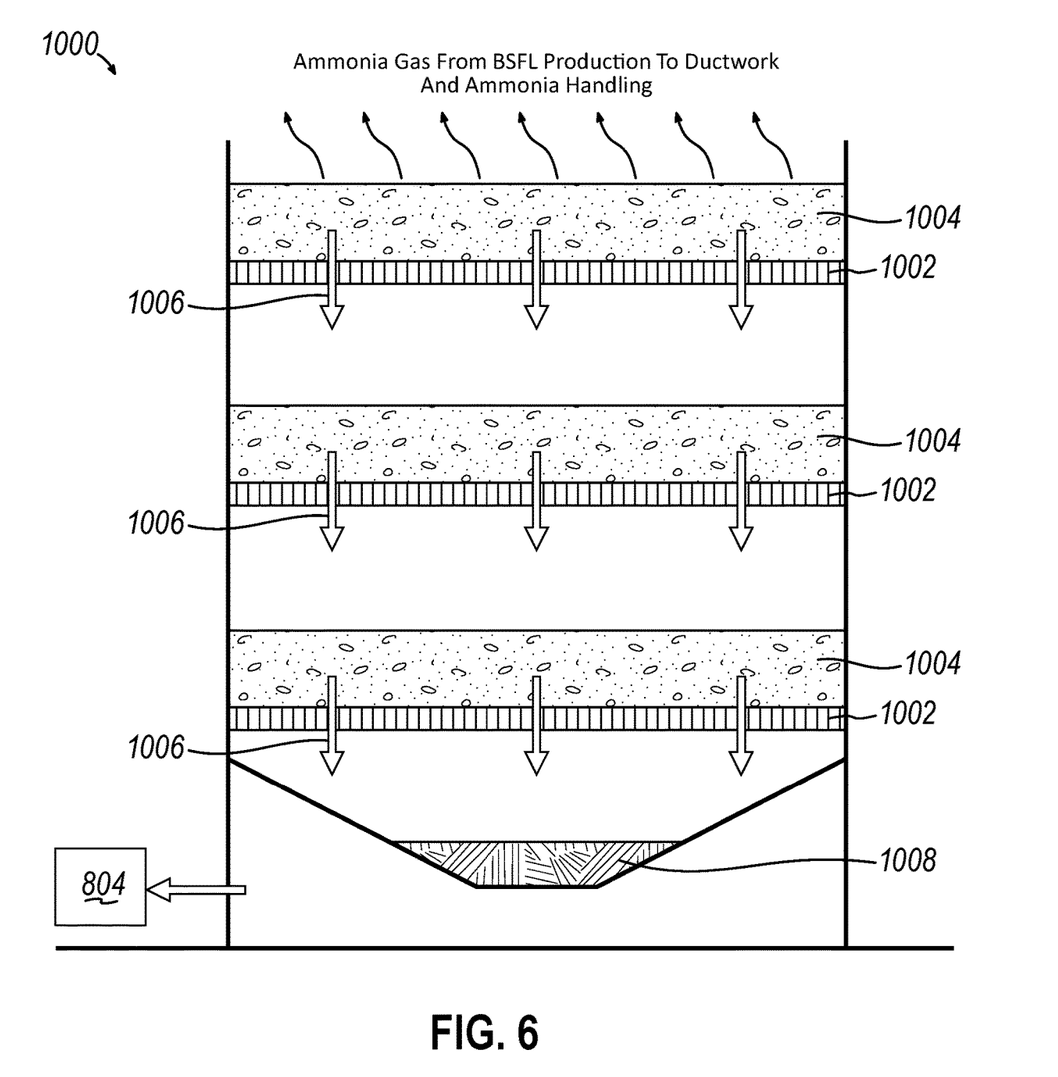
FIG. 6 is an example embodiment of one of the vertical growing cages utilized within the method of the present disclosure.

In one embodiment, each of the growing room(s) 302 are equipped with vertical growing cages, such as the cage 1000 shown in FIG. 6. Each level of each vertical growing cage may support a net layer 1002, such as a semipermeable mesh layer 1002 upon which the early-stage BSFL and feedstock 1004 are added. In the embodiments wherein the net layer 1002 is a semipermeable mesh layer, because the mesh layers are semipermeable, the leachate produced by the BSFL and the gravitational water 1006 from the feedstock on the upper levels of the vertical growing cage 1000 can percolate down through the mesh layers 1002 on to the lower layers of feedstock and BSFL 1004. As mentioned above, below the lowest level of the vertical growing cage 1000 can be a collection system 1008 which may collect this leachate and gravitational water and direct it to a storage tank, such as storage tank 804 discussed above, which can be located below the growing cages.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described to best illustrate principles of various embodiments as are suited to particular uses contemplated. The scope is, of course, not limited to the examples set forth herein, but can be employed in any number of applications and equivalent devices by those of ordinary skill in the art. Rather it is hereby intended for the scope of the present disclosure to be defined by the claims appended hereto.

What is claimed is:

1. A closed-loop method for the continuous production of biochar and nutrients, the method comprising:

placing high-moisture content feedstock and a source of black soldier flies within at least one breeding room to produce young black soldier fly larvae (BSFL);

placing high-moisture content feedstock and a first portion of the young BSFL within at least one growing room to produce leachate, mature BSFL, and frass;

removing the leachate from the at least one growing room and removing the mature BSFL and frass from the at least one growing room;

separating the mature BSFL from the frass;

processing the mature BSFL to produce dried BSFL, BSFL oil, BSFL meal, BSFL puree, or a combination thereof; and processing a first portion of the frass through a pyrolysis process to produce biochar and heat;

wherein the biochar can be utilized within the feedstock, within a second portion of the frass to be utilized as a frass end product, as a biochar end product, or a combination thereof; and wherein the heat can be utilized to heat the at least one breeding room, to heat the at least one growing room, to process the frass, or a combination thereof.

2. The method of claim 1, further comprising the step of cleaning the at least one growing room with water once the mature BSFL and frass have been removed from the at least one growing room such that effluent water is produced.

3. The method of claim 2, further comprising the step of treating the effluent water, and wherein the treated effluent water can be recycled and used to clean the at least one growing room.

4. The method of claim 3, wherein the biochar produced is cooled prior to being utilized within the feedstock, within a second portion of the frass to be utilized as a frass end product, and/or as a biochar end product.

5. The method of claim 4, wherein the biochar is cooled by being combined with leachate, treated effluent water, municipal water, or a combination thereof.

6. The method of claim 3, wherein the step of treating the effluent water utilizes a biochar-based filtration system, wherein biochar produced during the step of processing is the biochar used in the biochar-filtration system.

7. The method of claim 1, further comprising the step of removing ammonia from the at least one breeding room, the at least one growing room, or a combination thereof.

8. The method of claim 7, wherein the step of removing ammonia utilizes ductwork and pumps located within the at least one breeding room and the at least one growing room to pump the removed ammonia to a composting mound located adjacent the at least one breeding room and the at least one growing room.

9. The method of claim 8, wherein biochar produced during the step of processing the first portion of the frass can be incorporated into the composting mound.

10. The method of claim 1, wherein the at least one growing room is light controlled, temperature controlled, and humidity controlled; and wherein the at least one growing room includes a plurality of growing cages, wherein each said growing cage includes multiple vertically stacked levels, and wherein each level of the multiple vertically stacked levels includes a net layer upon which the high-moisture content feedstock and the first portion of the young BSFL are placed.

11. The method of claim 10, wherein the leachate produced within the at least one growing room percolates down through the net layer of each level of the multiple vertically stacked levels and into a collection system located below the plurality of growing cages; and wherein the collection system will send the leachate into a storage tank.

12. The method of claim 1, wherein, prior to undergoing the pyrolysis process, the step of processing the first portion of the frass further includes pressing or centrifuging the frass to remove any additional leachate and drying of the frass such that the frass has a moisture content of between about 15% to about 30% prior to pyrolysis.

13. The method of claim 12, wherein prior to drying the frass, the frass is combinable with external materials selected from the group consisting of organic materials, sawdust, woodchips, corrugated cardboard, and combinations thereof.

14. The method of claim 1, wherein the high-moisture content feedstock is industrial food processing waste materials selected from the group consisting of spent grains, wet distiller's grains, food waste/by-products, and combinations thereof.

15. The method of claim 1, wherein the source of black soldier flies can be black soldier fly eggs, young BSFL, adult black soldier flies, or combinations thereof.

16. The method of claim 1, wherein chicken feed is additionally placeable within the at least one breeding room.

17. The method of claim 1, wherein a second portion of the young BSFL will remain in the at least one breeding room to continue to produce young BSFL.

18. The method of claim 1, wherein the at least one breeding room is light controlled, temperature controlled, humidity controlled, or combinations thereof; and wherein the at least one breeding room includes a plurality of breeding cages, wherein each said breeding cage includes multiple vertically stacked levels, and wherein each level of the multiple vertically stacked levels includes a breeding tray upon which the high-moisture content feedstock and the source of black soldier flies are placed.

19. The method of claim 1, wherein a portion of the mature BSFL can be utilized as a live finished product.

20. The method of claim 1, wherein the step of processing the first portion of the frass through a pyrolysis process also produces condensable gases and non-condensable gases; and wherein the condensable gases and non-condensable gases are burned in a separate chamber along with oxygen to produce the heat.

* * * * *